United States Patent [19]

Daville

[11] 4,338,939

[45] Jul. 13, 1982

[54] INCONTINENCE PANTS

[76] Inventor: Helenne Daville, 1237 Admiral Dr., Apopka, Fla. 32703

[21] Appl. No.: 125,283

[22] Filed: Feb. 27, 1980

[51] Int. Cl.³ .......................................... A41B 13/02
[52] U.S. Cl. ..................................... 128/286; 128/288
[58] Field of Search ................ 128/286, 288, 295, 287

[56] References Cited

U.S. PATENT DOCUMENTS

| | | | |
|---|---|---|---|
| 26,939 | 8/1970 | Hervey et al. | 128/284 |
| 1,931,357 | 9/1933 | Potwin | 128/284 |
| 2,292,030 | 9/1942 | Kraft | 128/287 |
| 2,577,398 | 12/1951 | Blake | 128/287 |
| 2,755,804 | 7/1956 | Michael | 128/284 |
| 2,793,642 | 5/1957 | Andruhovici | 128/284 |
| 3,000,381 | 9/1961 | Mulhole et al. | 128/284 |
| 3,030,958 | 4/1962 | Levin | 128/294 |
| 3,693,621 | 9/1972 | Jarusik | 128/287 |
| 3,707,969 | 1/1973 | Sanford | 128/287 |
| 3,968,798 | 7/1976 | Hokanson | 128/284 |
| 4,022,210 | 5/1977 | Glassman | 128/284 |

*Primary Examiner*—James J. Bell
*Attorney, Agent, or Firm*—Ralph D'Alessandro

[57] ABSTRACT

Incontinence pants are provided to be worn by a person about the waist and about and between the legs having a supporting garment with front and back sides, retaining flaps affixed to both the front and the back sides, an absorbent disposable diaper and fasteners affixed to each pair of retaining flaps so human waste matter is retained by the diaper.

9 Claims, 9 Drawing Figures

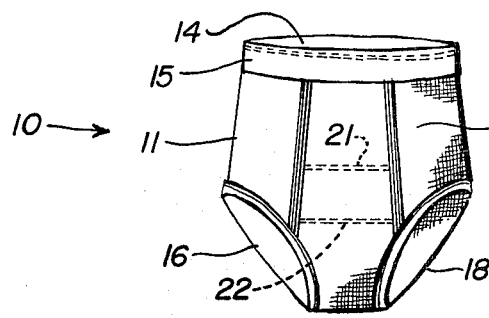
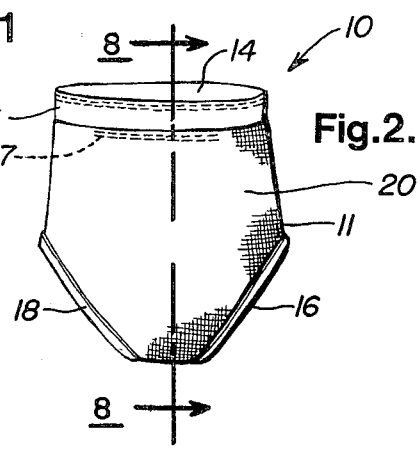
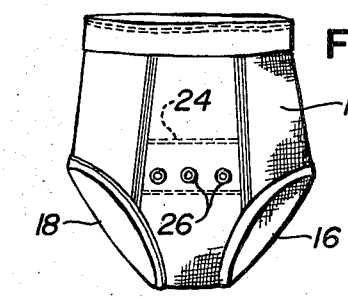
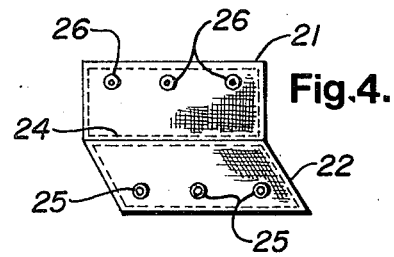
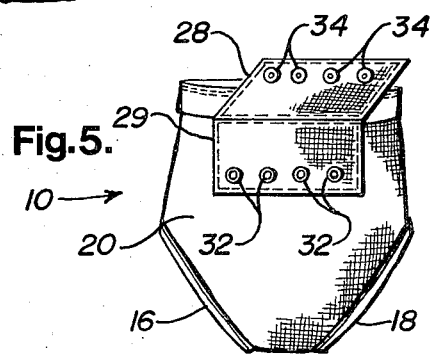
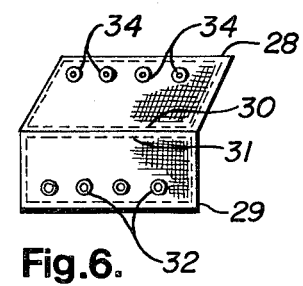
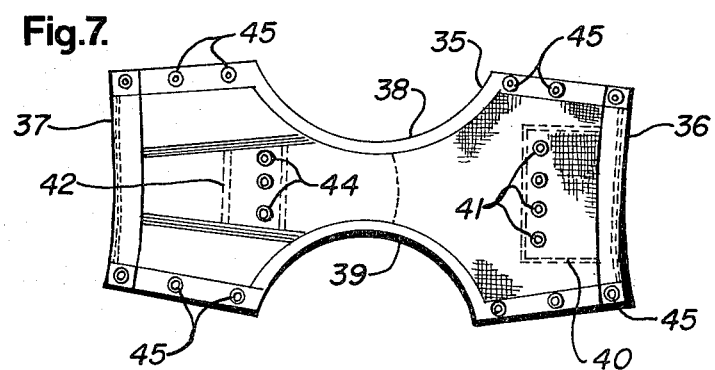

INCONTINENCE PANTS

BACKGROUND OF THE INVENTION

This invention is concerned with diaper systems and, more specifically with incontinence pants for elderly men and women who suffer from uncontrolled bladder and bowel discharge.

It has been the custom to provide geriatric patients with a variety of undergarments to collect the urine and fecal matter that results from the uncontrolled discharge of the bladder and the bowels. These garments have primarily attempted to preclude the passage of the human waste matter through to the outer clothes, without any effective way to prevent their being bulky, obvious to an observer and irritating to the sensitive skin of an elderly person. Most prior art has attempted to utilize devices which snap into position about the waist and have some sort of a fluid impervious outer sheet of material which contacts the skin at the waist and around the legs. These types of incontinence garments suffer from two major disadvantages. Because they must be drawn tightly about the legs to prevent leakage, they prevent air from passing easily through, essentially preventing the legs and genital area that is covered from breathing. Secondly, the skin of geriatric patients tends to be extremely sensitive and susceptible to sores from minimal abrasive contact. Incontinence pants of the type described have this effect.

Other types of garments have attempted to solve the problem by using absorbent pads that were somehow fastened to the inside of the supporting garment. One approach inserts the pad into a pair of pockets on opposing sides of the supporting garment. This has proven unsatisfactory, however, because the absorbent pad is not securely fastened to prevent its bunching up and either becoming uncomfortable for the wearer or nonfunctional for its original intended purpose. To remedy this deficiency another method utilizes zippers to fasten the absorbent pad or liner to the supporting garment. The zippers, however, also proved unsatisfactory since they can catch the skin and eventually induce a sore which causes some degree of bleeding. Various other absorbent pad retainers have been tried in attempts to solve this problem. All generally suffered from the problem of either irritating the skin of the wearer or permitting the absorbent pad to bunch up, thereby minimizing their protective worth.

Alternately, the use of rubber pants on patients or rubber liner sheets on beds cause the skin of elderly patients to become irritated or create bed sores from excessive moisture retention next to the skin.

The foregoing problems are solved in the incontinence pants of the present design by providing in a supporting garment a diaper retaining device that has two flaps or bands of cloth material fastened to the supporting garment and fastenable through the diaper via gripper snaps to retain the diaper loosely and yet securely in place resistant to fluid runoff and fecal matter escape while still giving ample coverage of the rectal area and maximum protection to the wearer.

SUMMARY OF THE INVENTION

It is a principal object of the present invention to provide an improved incontinence pants with a reuseable supporting garment and a disposable diaper that is held securely in place by diaper retainers so as to protect the wearer against the uncontrolled discharge of the bladder or the bowels.

It is another object of the present invention to provide incontinence pants that are equally well adapted to be worn by male or female geriatric patients.

It is a feature of this invention that the diaper is easily removed from the supporting garment for disposal after use while the supporting garment itself is readily reuseable after washing.

It is another feature of this invention that the supporting garment with its diaper retainers does not bind the skin of its wearer.

It is an advantage of this invention that the incontinence pants are low cost and simple in design.

It is another advantage of this invention that the need for rubber pants to be worn by the patient or rubber lining sheets on a bed is avoided.

It is a further disadvantage of this invention that the disposable diaper lining is held securely in position within the supporting garment by the diaper retainers in such a manner as to keep the fecal matter in minimal contract with the surface of the skin of the wearer and to retain urine in the front portion without permitting its runoff.

It is still another advantage of this invention that the incontinence pants are easily made in varying sizes to fit all size patients and are comfortable and not readily discernible when worn under clothing.

These and other objects, features and advantages are obtained by providing incontinence pants to be worn by a person about the waist and about and between the legs having a supporting garment with front and back sides, retaining flaps affixed to both the front and the back sides, an absorbent disposable diaper and fasteners affixed to each pair of retaining flaps so human waste matter is retained by the diaper.

BRIEF DESCRIPTION OF THE DRAWINGS

The advantages of this invention will become apparent upon consideration of the following detailed disclosure of the invention, especially when it is taken in conjunction with the accompanying drawings wherein:

FIG. 1 is a front elevational view of the incontinence pants without the disposable absorbent diaper showing in broken lines the front diaper retaining flaps or bands of cloth;

FIG. 2 is a rear elevational view of the incontinence pants without the disposable absorbent diaper showing in broken lines the point of attachment of the rear diaper retaining flaps or bands of cloth;

FIG. 3 is a front elevational view of the incontinence pants without the disposable absorbent diaper and with the supporting garment inside out showing the front diaper retaining flaps or bands of cloth with the gripper snaps which retain the diaper;

FIG. 4 is an elevational view of the front pair of diaper retaining flaps or bands of cloth showing the gripper snaps on each individual flap;

FIG. 5 is a rear elevational view of the incontinence pants without the disposable absorbent diaper and with the supporting garment inside out showing the positioning of the rear pair of diaper retaining flaps or bands of cloth with the gripper snaps which retain the diaper;

FIG. 6 is an elevational view of the rear pair of diaper retaining flaps or bands of cloth showing the gripper snaps on each individual flap;

FIG. 7 is a top plan view of an alternative embodiment of the incontinence pants showing the diaper retaining flaps or bands of cloth on a supporting garment which is snapped on and about a wearer's waist;

DETAILED DESCRIPTION

Figure 8:
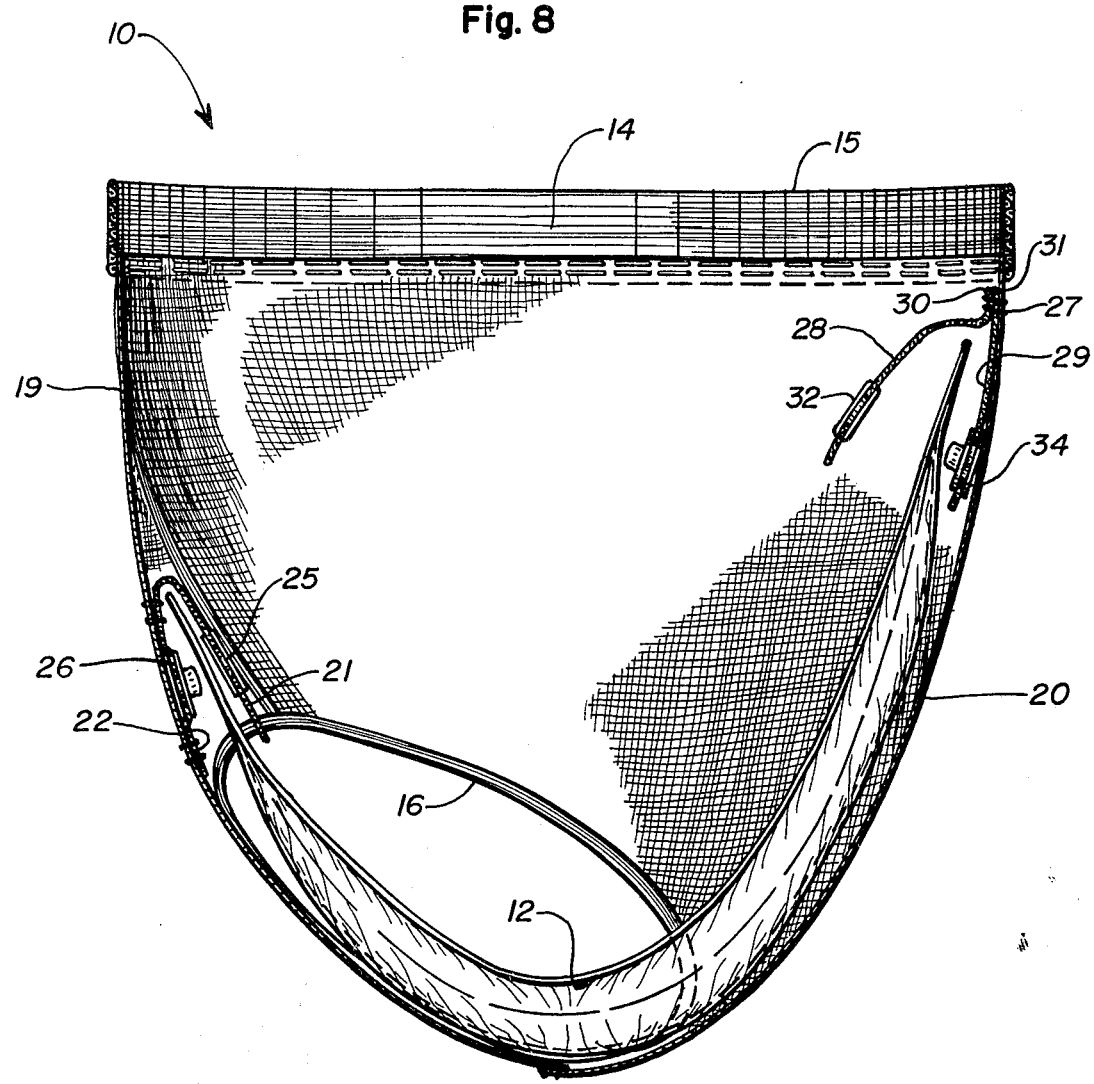
FIG. 8 is a side view taken along the section lines 8—8 of FIG. 2 showing the positioning of the disposable absorbent diaper between the pairs of flaps of the front and rear retaining flaps or bands of cloth prior to fastening via the gripper snaps.

FIG. 1 depicts the incontinence pants, indicated generally by the numeral 10, as seen from the front, while FIG. 2 shows the pants 10 as seen from the rear. The pants 10 comprise an outer supporting garment 11 and an inner disposable diaper 12, best seen in FIG. 8.

The supporting garment 11, as seen in FIGS. 1–4, has an expandable opening 14 at the waist with an expandable band 15, such as elastic, at the top. On the bottom are two generally circular openings 16 and 17, one for each leg of the wearer. The front side 19 and rear side 20 of the garment 11 are connected to form a generally continuous surface about the waist, hip and genital area of the wearer. The supporting garment 11 is of fabric content, preferably 50% cotton and 50% polyester knit to provide a soft, comfortable non-abrasive contacting surface with the skin. The supporting garment 11 is typically a pair of briefs or jockey style undershorts, commonly commercially available. Fastened to the front side 19 of the garment 11 generally in the center are a pair of diaper retaining flaps, or bands, 21 and 22 respectively. The flaps 21 and 22 are generally rectangularly shaped and composed of the same type of fabric as the supporting garment 11. Flap 22, best seen in FIGS. 3 and 4, is sewn along only its top border 24 so that it can be raised and lowered in hinged fashion from flap 22. Appropriately fastened into flap 22 of FIG. 4 are a plurality of female gripper snaps 25. Snaps 25 matingly join with a corresponding number of male gripper snaps 26 appropriately fastened into flap 21. This arrangement thus permits the disposable baby diaper 12, which is readily available from a number of manufacturers, such as Johnson and Johnson or Proctor and Gamble, in toddler size, to be inserted between the flaps and secured therebetween by the fastening of the snaps therethrough. This retaining technique is possible because of the relatively soft absorbent material in the diaper 12 and its easily puncturable liquid impervious outer covering.

In similar fashion the rear side 20 of the garment 11 has in FIG. 5 a pair of flaps 28 and 29. Flaps 28 and 29 are sewn into the fabric material along only their respective top borders 30 and 31. Flap 29 has a plurality of female gripper snaps 32 appropriately fastened therein while flap 30 has a corresponding number of male gripper snaps appropriately fastened therein. An edge of diaper 12 is inserted between the flaps 28 and 29 and is secured as described above by the squeezing together of the gripper snaps 32 and 33. Rear flaps 28 and 29 are secured to the supporting garment 11, such as by sewing, along their top borders 30 and 31 respectively, seen briefly in FIG. 2 as stitching 27, to permit the diaper 12 to be able to move while the wearer moves about without binding or pinching the skin. Flaps 28 and 29 are long enough to span the side to side reach of a toddler's sized diaper and extend from top to bottom approximately 4 inches.

Both pairs of flaps, front flaps 21 and 22 and rear flaps 28 and 29, can have stitched borders to prevent unraveling of the fabric and to provide a uniform border. Additionally, the front flaps 21 and 22 should be of sufficient length to generally stretch and support the disposable diaper 12 across the pelvic region. Front flaps 21 and 22 are approximately 2 inches deep in their preferred form.

An alternative embodiment is shown in FIG. 7 wherein the supporting garment 35 is designed to be placed under a bed-ridden patient and then folded up and about the waist where it is securely fastened in place. Garment 35 has a front top 37 and a back top 36 which combine to form an opening for the waist when fastened together. The garment 35 is tapered to provide a left leg opening 39 and a right leg opening 38 when the front and back portions are fastened together. Attached in the manner and fashion previously described are a pair of rear flaps 40. Flaps 40 have a plurality of the previously described mated gripper snaps 41 fastened to them. A pair of front flaps 42 are attached to the garment 35 also in the manner and fashion previously described. Flaps 42 also have a plurality of the previously described gripper snaps fastened to them. The garment 35 also has a plurality of fasteners 45 along the edges of its sides to permit it to be fastened closed about the waist of the patient after the garment 35 has been folded to form a covering garment. The fasteners 45 typically are the paired male and female gripper snaps previously described.

Figure 9:
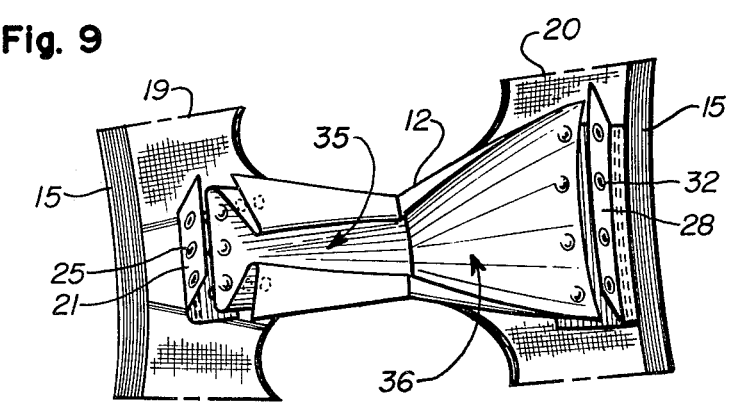
FIG. 9 is a top plan view of the incontinence pants illustrating how the diaper is folded in place within the supporting garment which is diagrammatically slit open along both sides and laid flat to show the urine pocket and the fecal matter trap for retaining human waste matter.

In use, the incontinence pants 10 are readied for wearing by taking a disposable diaper 12 and inserting the diaper's front top edge between the flaps 21 and 22. The diaper 12 is folded so that its full folded width is approximately 5 inches across the front. The diaper 12 is held in position by the flaps 21 and 22 above the front of the pelvis of the wearer. The male gripper snaps 26 are pressed firmly into the female gripper snaps 25, thereby causing the male gripper snaps 26 to individually penetrate the diaper 12 and seat themselves within the female gripper snaps 25. The bands of cloth of the flaps 21 and 22 and the thusly mated gripper snaps serve to securely hold the diaper 12 in its folded configuration. The procedure is repeated for the diaper's rear top edge with flaps 28 and 29 and gripper snaps 32 and 34 so that the diaper's rear top edge is stretched to its full width, or approximately 13 inches in end to end length. The diaper 12, which is preferably toddler sized, is thus folded in the front to form two pleats which provide a urine pocket 35 in the front and a fecal matter trap 36, as seen in FIG. 9, in the rear that will hold fecal matter away from the skin and increase the urine retaining surfaces available. This configuration will prevent the seepage of urine back to the area of the base of the spine of the wearer and thus prevent the occurrence of painful urine sores or bed sores in this area.

Once thusly assembled, the pants 10 are pulled up and about the wearer's waist by placing each foot through the appropriate leg opening 16 or 18. As worn, the wearer of the incontinence pants 10 has free, unrestricted movement without the discomfort and fear of an untimely discharge of waste matter.

Further, the length of the diaper 12 is uniformly maintained when worn as approximately 6 inches from the base of the crotch of the wearer to the top of the front flaps 21,22 and approximately 12 inches from the base of the crotch of the wearer to the top of the rear of the diaper 12 by adjusting the position of the snaps on the flaps 21,22 and 28,29, or alternately by varying the length of the flaps 21,22 and flaps 28,29 by selecting their respective points of sewn attachment to the supporting garment 11.

While the preferred structure in which the principles of the present invention have been incorporated is shown and described above, it is to be understood that the invention is not to be limited to the particular details thus presented, but, in fact, widely different means may be employed in the practice of the broader aspects of this invention. The scope of the appended claims is intended to encompass all obvious changes in the details, materials and arrangement of parts which will occur to one of skill in the art upon a reading of this disclosure.

Having thus described the invention, what is claimed is:

1. Incontinence pants adapted to be worn with a human waste absorbing disposable diaper by a person about the waist and between the legs by being pulled on over the legs comprising:
   (a) a unitary supporting garment of fabric content having an upper portion and a lower portion, the upper portion having a first expandable opening to surround the waist, the lower portion having a second and a third opening each adapted to receive a leg therethrough;
   (b) an intermediate portion connecting the upper portion and the lower portion and having a front side and an opposing rear side both interconnected to form with the upper portion a continuous surface, the continuous surface having a midline that passes centrally through the front side and the opposing rear side;
   (c) first diaper retaining means fastened to the front side having an inner flap and an outer flap and positioned at least partially along the midline;
   (d) at least a second diaper retaining means fastened to the continuous surface on the opposing rear side having an inner flap and an outer flap and positioned at least partially along the midline; and
   (e) coupling means fastened to the inner and outer flaps of the first and second diaper retaining means so as to permit each diaper retaining means to receive between the inner and outer flaps the disposable diaper and to detachably hold the disposable diaper therebetween such that a fecal matter trap is formed between the legs of the wearer and a urine pocket is formed adjacent the front portion of the supporting garment when the disposable diaper is positioned between the wearer's legs and up and about at least a portion of the front and the back of the waist effective to retain human waste when the supporting garment is pulled up and about the waist.

2. The incontinence pants according to claim 1 wherein the coupling means further comprise a plurality of male and female interlocking snaps, the male snaps being on the outer flap and the female snaps being on the inner flap such that when the disposable diaper is placed therebetween the male snap passes through the disposable diaper and is received and retained by the female snap.

3. The incontinence pants according to claim 1 wherein the coupling means further comprise a plurality of male and female interlocking snaps, the male snaps being on the inner flap and the female snaps being on the outer flap such that when the disposable diaper is placed therebetween the male snap passes through the disposable diaper and is received and retained by the female snap.

4. The incontinence pants according to claim 1 wherein the upper portion comprises an expandable elastic band that does not bind the skin.

5. The incontinence pants according to claim 4 wherein the fabric content is approximately equal parts of cotton and polyester knit.

6. Incontinence pants to be worn by a person about the waist and about and between the legs by being pulled on over the legs comprising:
   (a) a unitary supporting garment of predetermined fabric content having an upper portion and a lower portion, the upper portion having a first opening to surround the waist, the lower portion having a second and third opening each adapted to receive a leg therethrough;
   (b) an intermediate portion connecting the upper portion and the lower portion and having a front side and an opposing rear side both interconnected to form with the upper portion a continuous surface;
   (c) first diaper retaining means fastened to the front side having an inner flap and an outer flap;
   (d) at least a second diaper retaining means fastened to the continuous surface on the opposing rear side having an inner flap and an outer flap;
   (e) absorbent diaper means having an inner fluid absorbing surface and an outer fluid impervious surface adjacent the continuous surface and having opposing edges extending the length of the absorbent diaper, the edges being elevated from the plane of the inner fluid absorbing surface to thereby form a depressed area for retaining waste matter, the diaper means further being insertable between the inner flaps and outer flaps of the first and second diaper retaining means; and
   (f) coupling means fastened to the inner and outer flaps of the first and second diaper retaining means so as to permit each diaper retaining means to receive between the inner and outer flaps the absorbent diaper and to detachably hold the absorbent diaper therebetween such that a fecal matter trap is formed between the legs of the wearer and a urine pocket is formed adjacent the front portion of the supporting garment in the depressed area of the diaper means when the supporting garment is pulled up and about the waist to retain human waste matter.

7. The incontinence pants according to claim 6 wherein the coupling means further comprise a plurality of male and female interlocking snaps, the male snaps being on the outer flap and the female snaps being on the inner flap such that when the disposable diaper is placed therebetween the male snap passes through the disposable diaper and is received and retained by the female snap.

8. The incontinence pants according to claim 7 wherein the upper portion comprises an expandable elastic band that does not bind the skin.

9. The incontinence pants according to claim 8 wherein the fabric content is approximately equal parts of cotton and polyester knit.

* * * * *